US012321667B2

(12) United States Patent
Szyman et al.

(10) Patent No.: US 12,321,667 B2
(45) Date of Patent: Jun. 3, 2025

(54) CONTACTLESS CONTROL OF PHYSIOLOGICAL MONITORS

(71) Applicant: Becton, Dickinson and Company, Franklin Lakes, NJ (US)

(72) Inventors: Catherine M. Szyman, Westlake Village, CA (US); Ryan Timothy McHale, Tustin, CA (US); Ryan James Hastings, Newport Beach, CA (US); Christina Gin Teng Chen, Lake Forest, CA (US); Sungwhan Cha, Lake Forest, CA (US); Kenneth William Sprague, Irvine, CA (US); Sara Mohiba Boukai, Coto de Caza, CA (US); Fabian Guot Ngo, Santa Ana, CA (US)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 0 days.

(21) Appl. No.: 18/352,161

(22) Filed: Jul. 13, 2023

(65) Prior Publication Data
US 2024/0020092 A1 Jan. 18, 2024

Related U.S. Application Data

(60) Provisional application No. 63/389,153, filed on Jul. 14, 2022.

(51) Int. Cl.
G06F 3/16 (2006.01)
A61B 5/00 (2006.01)
(Continued)

(52) U.S. Cl.
CPC ............. *G06F 3/167* (2013.01); *A61B 5/746* (2013.01); *A61B 5/749* (2013.01); *G06F 3/013* (2013.01);
(Continued)

(58) Field of Classification Search
None
See application file for complete search history.

(56) References Cited

U.S. PATENT DOCUMENTS 5,417,210 A 5/1995 Funda et al.
5,544,654 A 8/1996 Murphy et al.
(Continued)

OTHER PUBLICATIONS

Christian F. Poets, "Pulse oximetry vs. transcutaneous monitoring in neonates: practical aspects" acutecaretesting.org, Oct. 2003.

*Primary Examiner* — Dorothy Harris
(74) *Attorney, Agent, or Firm* — Dority & Manning, P.A.

(57) ABSTRACT

Systems and methods for contactless control of a physiological monitor are provided. A number of systems utilize an input device for audio-based control of a physiological monitor and/or an input device for gesture-based control of a physiological monitor. Many systems process audio (e.g., voice) or gesture commands to direct a physiological monitor to perform actions, such as begin monitoring, silencing an alarm, changing parameters, navigating screens and/or menus, and/or any other function. Such contactless systems reduce or eliminate physical contact with a physiological monitor, which can mitigate contamination between patients or individuals, which can occur via traditional systems.

32 Claims, 3 Drawing Sheets

(51) Int. Cl.
*G06F 3/01* (2006.01)
*G06T 7/593* (2017.01)
*G06V 10/20* (2022.01)

(52) U.S. Cl.
CPC .............. *G06F 3/017* (2013.01); *G06T 7/593* (2017.01); *G06V 10/255* (2022.01)

(56) References Cited

U.S. PATENT DOCUMENTS

| | | |
|---|---|---|
| 6,278,975 B1 | 8/2001 | Brant et al. |
| 7,058,204 B2 | 6/2006 | Hildreth et al. |
| 7,136,710 B1 | 11/2006 | Hoffberg et al. |
| 7,319,962 B2 | 1/2008 | Goedeke et al. |
| 7,379,563 B2 | 5/2008 | Shamaie |
| 7,620,553 B2 | 11/2009 | Wang et al. |
| 7,698,002 B2 | 4/2010 | Music et al. |
| 7,921,017 B2 | 4/2011 | Claus et al. |
| 7,925,511 B2 | 4/2011 | Li et al. |
| 8,010,368 B2 | 8/2011 | Yamaki |
| 8,015,014 B2 | 9/2011 | Wang et al. |
| 8,160,683 B2 | 4/2012 | Shah et al. |
| 8,224,651 B2 | 7/2012 | Wang et al. |
| 8,502,876 B2 | 8/2013 | Wang et al. |
| 9,060,674 B2 | 6/2015 | Amling |
| 9,152,376 B2 | 10/2015 | Johnston et al. |
| 9,229,533 B2 | 1/2016 | Shigeta et al. |
| 9,274,608 B2 | 3/2016 | Katz et al. |
| 9,342,145 B2 | 5/2016 | Moffett |
| 9,514,746 B2 | 12/2016 | Wang et al. |
| 9,536,135 B2 | 1/2017 | Zhang et al. |
| 9,545,287 B2 | 1/2017 | Tashiro |
| 9,563,186 B2 | 2/2017 | Steinle et al. |
| 9,595,171 B2 | 3/2017 | Hurtig et al. |
| 9,625,993 B2 | 4/2017 | Merschon et al. |
| 9,785,228 B2 | 10/2017 | Schwesinger et al. |
| 9,829,984 B2 | 11/2017 | Dai et al. |
| 9,886,769 B1 | 2/2018 | Tremaine et al. |
| 9,911,166 B2 | 3/2018 | Reid et al. |
| 9,911,398 B1* | 3/2018 | McQueen ............ G06F 3/0481 |
| 9,990,050 B2 | 6/2018 | Zhang et al. |
| 10,368,836 B2 | 8/2019 | Merritt et al. |
| 10,403,402 B2 | 9/2019 | Ziraknejad et al. |
| 10,492,981 B1* | 12/2019 | Kumar ................. A61H 19/44 |
| 10,613,637 B2 | 4/2020 | Goetz et al. |
| 10,720,237 B2 | 7/2020 | Dobai et al. |
| 10,809,970 B2 | 10/2020 | Almendro Barreda et al. |
| 11,020,062 B2 | 6/2021 | Wagner et al. |
| 11,126,270 B2 | 9/2021 | Goetz et al. |
| 11,272,991 B2 | 3/2022 | Ziraknejad et al. |
| 11,347,316 B2 | 5/2022 | Goetz et al. |
| 2004/0193413 A1 | 9/2004 | Wilson et al. |
| 2009/0177477 A1* | 7/2009 | Nenov ............... G10L 15/1815 704/E15.04 |
| 2009/0315869 A1* | 12/2009 | Sugihara ............ H04N 1/00352 345/204 |
| 2010/0100080 A1 | 4/2010 | Huculak et al. |
| 2012/0249443 A1* | 10/2012 | Anderson ............. A63F 13/213 345/173 |
| 2014/0049465 A1 | 2/2014 | Tremaine et al. |
| 2014/0122059 A1* | 5/2014 | Patel ...................... G06F 16/40 704/235 |
| 2014/0297287 A1* | 10/2014 | Newman ................ G10L 25/93 704/275 |
| 2016/0132290 A1* | 5/2016 | Raux ...................... G06F 3/167 704/275 |
| 2017/0011210 A1* | 1/2017 | Cheong ................. A61B 5/681 |
| 2017/0020627 A1* | 1/2017 | Tesar ................... A61B 90/361 |
| 2018/0165854 A1* | 6/2018 | Du ........................ G06F 16/00 |
| 2018/0350360 A1* | 12/2018 | Knudson ................ G10L 25/51 |
| 2019/0121610 A1* | 4/2019 | Olsovsky ............... G06F 3/167 |
| 2019/0206396 A1* | 7/2019 | Chen ...................... G06F 3/167 |
| 2019/0370636 A1* | 12/2019 | Isopoussu ............. G06F 9/5077 |
| 2019/0392858 A1* | 12/2019 | Lee ......................... G10L 17/26 |
| 2020/0319705 A1* | 10/2020 | Rohrbacher ........ G06F 3/04842 |
| 2021/0345893 A1* | 11/2021 | Bishop ................... G16H 20/40 |
| 2023/0390653 A1* | 12/2023 | Usi ....................... G06F 16/215 |

\* cited by examiner

CONTACTLESS CONTROL OF PHYSIOLOGICAL MONITORS

CROSS-REFERENCE TO RELATED APPLICATIONS

The current application claims priority to U.S. Provisional Patent Application No. 63/389,153, filed Jul. 14, 2022, entitled "Contactless Control of Physiological Monitors" to Szyman, et al.; the disclosure of which is hereby incorporated by reference in its entirety.

FIELD OF THE INVENTION

The present invention generally relates to systems for controlling physiological monitors without physical contact of such devices; more specifically, devices and systems that utilize voice and/or gestures to control to allow control of a physiological monitor.

BACKGROUND OF THE INVENTION

Physiological monitors are important pieces of equipment for hospitals, medical clinics, and other medical facilities. Such monitors can be used for many purposes, including blood pressure, heart rate, blood oxygen, brain activity, and any other physiological measurement. While physiological monitors are necessary pieces of equipment, the use of buttons, knobs, and switches to control a monitor creates an avenue for contamination, cross-contamination, and nosocomial infections. Thus, there is a need for monitors that reduce or eliminate points of contact to reduce the risk of contamination.

BRIEF SUMMARY OF THE INVENTION

Many implementations are directed to systems and methods for artificial intelligence enabled control of hemodynamics and anesthesia in surgery patients and applications thereof.

In some aspects, the techniques described herein relate to a contactless physiological monitor, including a contactless input device capable of obtaining audio or motion-based data from a user, a processor, and a memory including instructions to direct the processor to obtain a contactless input from the user via the contactless input device, process the contactless input into a command, and take action by the processor based on the command.

In some aspects, the techniques described herein relate to a system, where the contactless input device obtains audio input from the user.

In some aspects, the techniques described herein relate to a system, where the contactless input device is a microphone.

In some aspects, the techniques described herein relate to a system, where the memory further includes instructions to process an audio signal into a voice command.

In some aspects, the techniques described herein relate to a system, where the memory further includes instructions to preprocess the audio signal.

In some aspects, the techniques described herein relate to a system, where the instructions to preprocess the signal includes removing background noise from the audio signal.

In some aspects, the techniques described herein relate to a system, where the contactless input device is a camera.

In some aspects, the techniques described herein relate to a system, where the camera is a 2D camera.

In some aspects, the techniques described herein relate to a system, where the camera is a 3D camera.

In some aspects, the techniques described herein relate to a system, where the memory further includes instructions to direct the processor to perform depth measurement.

In some aspects, the techniques described herein relate to a system, where the memory further includes instructions to direct the processor to process a gesture-based input from the user.

In some aspects, the techniques described herein relate to a system, where the instructions to process a gesture-based input from the user includes object recognition.

In some aspects, the techniques described herein relate to a system, where the memory further includes instructions to direct the processor to perform eyeball tracking.

In some aspects, the techniques described herein relate to a system, where the contactless input device is a LiDAR system.

In some aspects, the techniques described herein relate to a system, where the memory further includes instructions to direct the processor to process a gesture-based input from the user.

In some aspects, the techniques described herein relate to a system, where the instructions to process a gesture-based input from the user includes object recognition.

In some aspects, the techniques described herein relate to a system, where the memory further includes instructions to direct the processor to perform depth measurement.

In some aspects, the techniques described herein relate to a system, further including a sensor capable of obtaining a physiological measurement from an individual.

In some aspects, the techniques described herein relate to a system, further including a display to display data obtained from the sensor.

In some aspects, the techniques described herein relate to a system, further including an alarm.

In some aspects, the techniques described herein relate to a method, including obtaining a contactless input from a medical practitioner, processing the contactless input to identify a command from the medical practitioner, performing the command identified from the contactless input, In some aspects, the techniques described herein relate to a method, where the contactless input is selected from audio input and gesture input.

In some aspects, the techniques described herein relate to a method, where the contactless input includes a triggering input and a command input, where the triggering input identifies that the command input will follow, and the command input provides a desired action.

In some aspects, the techniques described herein relate to a method, further including preprocessing the contactless input.

In some aspects, the techniques described herein relate to a method, where preprocessing the contactless input includes removing background noise from an audio signal.

In some aspects, the techniques described herein relate to a method, where the contactless input is gesture input and where processing the contactless input includes performing a depth measurement on the gesture input.

In some aspects, the techniques described herein relate to a method, where the contactless input is gesture input and where processing the contactless input includes recognizing an object in the gestures input.

In some aspects, the techniques described herein relate to a method, where the contactless input is gesture input and where processing the contactless input includes performing eyeball tracking.

In some aspects, the techniques described herein relate to a method, where the command identified from the contactless input is selected from change screens, configure parameters, configure alarm target ranges, silence alarms, create new patient session, input patient demographics, start monitoring, stop monitoring, calibrate, read out current parameters, scroll, adjust volume, set a timer, set a reminder, and display patient summary.

Additional implementations and features are set forth in part in the description that follows, and in part will become apparent to those skilled in the art upon examination of the specification or as may be learned by the practice of the disclosure. A further understanding of the nature and advantages of the present disclosure may be realized by reference to the remaining portions of the specification and the drawings, which form a part of this disclosure.

BRIEF DESCRIPTION OF THE DRAWINGS

The description will be more fully understood with reference to the following figures, which are presented as exemplary implementations of the invention and should not be construed as a complete recitation of the scope of the invention, wherein.

DETAILED DESCRIPTION OF THE INVENTION

Figure 1:
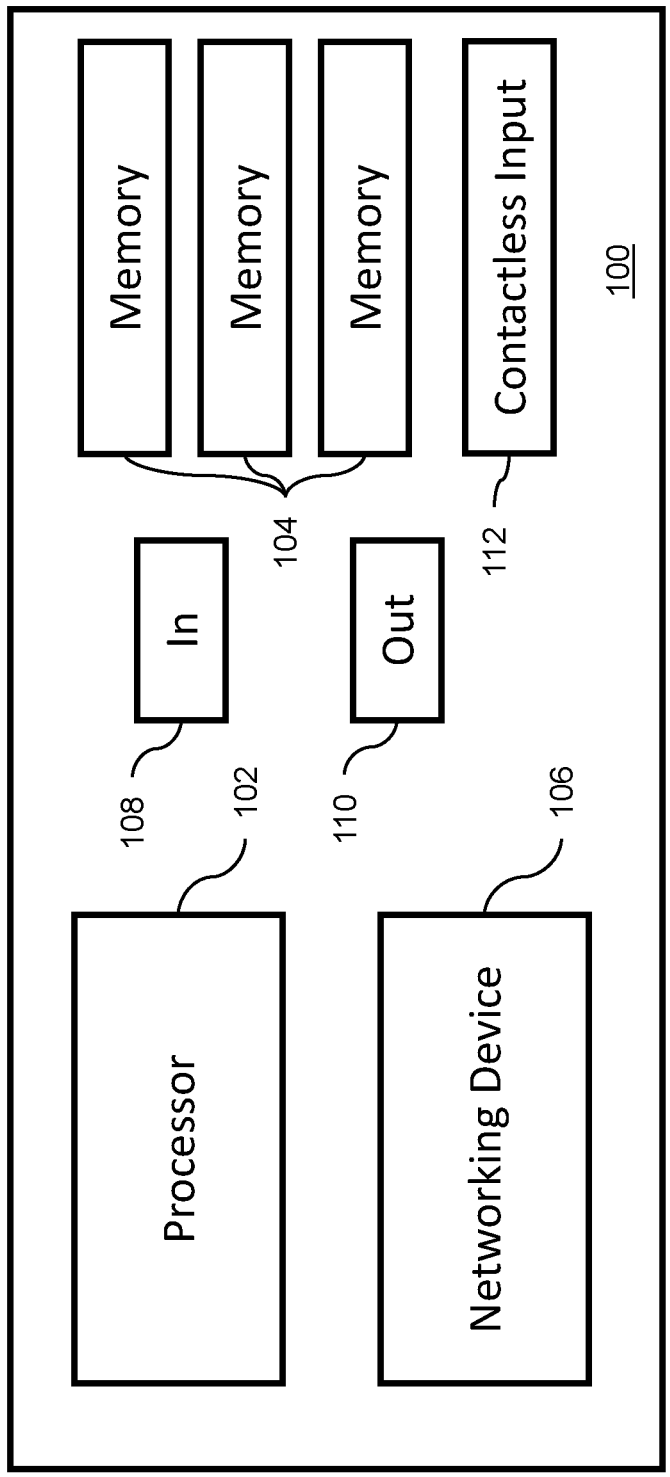
FIG. 1 illustrates a block diagram of exemplary components of a physiological monitoring system in accordance with various implementations.

Turning now to the drawings, systems for contactless control of physiological monitors are provided. Many systems described use one or more of voice and gesture control to control a physiological monitor. Voice control can use microphones to obtain a voice or other sound input from a user (e.g., doctor, physician, nurse, or other medical practitioner). Gesture control can utilize one or more cameras, LiDAR, or other optical sensor to obtain gesture information from a practitioner. Many systems incorporate software (including artificial intelligence based software) to perform voice recognition or gesture recognition for a voice command or gesture and/or to translate such command or gesture into input for a monitor.

Major challenges in controlling devices includes inputs that are intuitive, unambiguous, and simple. For example, inputs that involve elaborate or intensive motions or commands may be difficult to perform or remember during procedures, leading to non-use of voice- and/or gesture-controlled devices and obviating any benefits thereof. Additionally, voice and/or gesture commands that sound like or appear like other commands could lead to an incorrect input or selection.

Contactless Control

Many systems utilize voice and/or gesture commands to perform functions on a physiological monitor. Many commands are intuitive and convenient to cover the most common and useful inputs for a physiological monitor. Such commands include (but are not limited to) change screens (e.g., trends versus tabular), configure parameters, configure alarm target ranges, silence alarms, create new patient session, input patient demographics, start monitoring, stop monitoring, calibrate, read out current parameters, scroll (e.g., back or forward), adjust volume, set a timer, set a reminder, display patient summary, and/or any other common or routine function. Additional systems include troubleshooting commands to allow for problem solving or other issues when setting up or during a procedure, including alarm information, parameter display, setup swan, setup CS, setup FT, and/or other areas where troubleshooting may be relevant. Certain systems also accept commands to identify which options or capabilities are available, such as if a practitioner needs a reminder of which commands are currently available (e.g., in case of a hierarchical system, where one command leads to a limited set of other commands, including "troubleshooting→setup Swan→selecting parameters;" "adjust volume→volume level;" etc.).

When input is processed into a specific command for a physiological monitor, certain systems provide a signal or other confirmation after receiving a command or processing a command. Various systems provide an audio and/or visual confirmation. Audio confirmations include a tone and/or a spoken confirmation (e.g., a word such as "received" or repeat of the command). Some systems provide two audio confirmations, such as to note receipt of a command and confirmation that the command is processed. Similarly, visual confirmations can include a light or non-specific visual signal on a screen and/or a visual repeat of the command via text display on a screen. Additionally, some systems provide notice that a command was not interpreted or could not be processed, such as if the command does not make sense in the context of the procedure, is impossible given the configuration, and/or if the command could not be interpreted. Certain systems provide trouble shooting issues, if the command is not possible (e.g., to connect a sensor, if the sensor is not detected, etc.). Once a command is processed, some embodiments provide the specific output (e.g., cardiac output, blood pressure, etc.) as a confirmation that the command was received and processed. Additional systems may provide a confirmation that a command is being received, such that once a command starts, an audio or visual notice may be provided to indicate the physiological monitor is receiving the command (e.g., voice and/or gesture).

Various systems allow for alternative commands for the same process. For example, to silence an alarm a practitioner could use commands such as "silence," "silence alarm," "stop alarm," "stop beeping," and/or any other similar phrasing to silence an alarm. It should be noted that the example regarding an alarm is merely exemplary, and alternative commands may be used for various additional processes.

Certain systems utilize a triggering action or input as a signal that additional input is forthcoming. For example, a phrase like "Hey Eddy . . ." or a gesture such as eye contact with the monitor or holding up a palm may turn the machine into "listen" or "observe" mode to identify input as a true command versus other noise or motion within the exam room, operating room, or other medical facility. At certain times, a monitor may trigger itself to identify a command, such as an alarm, where the next action is to silence the alarm and/or take an action to rectify the reason for the alarm.

Voice Command

Many physiological monitors provided by this disclosure include voice control. Many of these systems include a microphone or other sound detector to obtain voice commands or other sound input from an operator (e.g., physician, clinician, nurse, and/or other medical professional).

Exemplary microphones can include dynamic microphones, condenser microphones, ribbon microphones, and/or other type of microphone. Certain physiological monitors include multiple microphones (e.g., 2, 3, 4, or more microphones) for redundancy, backup, stereo input, or any other reason where more than one microphone could be beneficial.

When a voice command is performed by a practitioner, certain exemplary systems preprocess the audio data, such as to remove background sounds, filter out noise, isolate certain wavelengths or tones, and/or any other type of preprocessing. Once the vocal command is preprocessed, voice recognition can occur.

Certain systems perform audio recognition on voice commands as to translate a command or sound into an actual command to be performed by the physiological monitor. Many pieces of software are known in the art that can perform such recognition.

Gesture Command

Additional systems utilize gesture input from a practitioner to initiate commands or processes for a physiological system. Many of such systems include an input device to obtain video or visual input. Such input can include a camera (still and/or video), LiDAR system, and/or any other ability to obtain such input. Cameras used in systems can include cameras that obtain images in the visual spectrum (e.g., about 380 nm to about 750 nm or a subset thereof), while some systems use infrared cameras (e.g., about 700 nm to about 1 mm or a subset thereof). Some systems utilize 2D cameras, while additional systems utilize 3D cameras to obtain depth or distance information from a device. In certain systems, including systems implementing LiDAR, a projector is used to monitor the area, such as an infrared projector to provide a grid or other pattern to allow for tracking or observation of motions within an exam room, operating room, emergency room, or other clinical theater.

Certain systems utilize a reflector, retroreflector, or other type of device that can be used for tracking a particular part of a practitioner (e.g., head, hand, arm, etc.). Such devices can be attached to a glove, coat, face shield, mask, or other piece of a clothing or protective equipment.

"Gestures" used in various systems can include motion or be stationary positions in various physiological monitors, such that some gestures can include a swiping motion, shaking motion, or holding a hand position for a period of time. For example, a swiping motion can change switch screens, while a stationary finger over the mouth can be used to silence an alarm. Additional gestures can be used as input for various physiological monitors. Characteristics of gestures include ease of performing and deliberateness (e.g., gestures not likely to be performed accidentally).

Some systems are capable of eyeball tracking. Eyeball tracking can be used to move a cursor or pan (or scroll) across information on a screen, while a pause (for a minimum amount of time) in eyeball movement may indicate selecting a particular option. In some systems, a pause may trigger a zoom feature to enlarge a portion of a screen. Eyeball tracking can be contextual, based what in on the screen and/or where the eyeballs are looking—for example, certain points on the screen may be used for input or selection, while looking at other areas of the screen (e.g., charts or data) may trigger a zoom function. In certain systems, a cursor or cursor-like system may be employed to provide feedback to the practitioner about where they are looking. A cursor or cursor-like system can include a circle, dot, point, arrow, or other selector to indicate a single point on the screen, while other cursor-like systems can be a box or a highlight to indicate a certain area or position on the screen.

Using depth tracking, certain systems can change screens, modes, or other display, based on proximity of a practitioner to the monitor. For example, when a practitioner is performing a procedure, they are likely to be further from the monitor. As such, the system may default to displaying cardiac metrics of a patient, such as blood pressure, mean arterial pressure, cardiac output, etc., while when closer to the monitor, the system may display a startup screen, results summary, or other parameters that may be relevant before or after a procedure.

Software included in various systems are able to process motion or gesture input as provided by a practitioner and received by the system. Some software can track eyeballs via a camera or other visual input system. As noted herein, depending on the input device (e.g., 2D camera, 3D camera, LiDAR, etc.) the software can identify depth/distance of a practitioner, object recognition/identification (e.g., to identify a hand, face, arm, etc.) used for a gesture, gestures from the individual, eyeball tracking, and/or any relevant gesture-based input for the system.

Systems

Many systems of physiological monitors can include a variety of components for performing monitoring of an individual (e.g., patient) as well as obtaining contactless inputs from a user (e.g., physician, nurse, doctor, clinician, etc.). Turning to FIG. 1, an exemplary physiological monitor is illustrated. However, it should be noted that one skilled in the art will recognize that physiological monitors or systems may include other components that are omitted for brevity without departing from the scope of this disclosure.

In FIG. 1, a physiological monitor 100 can include a processor 102 and at least one memory 104. Memory 104 can be a non-volatile memory and/or a volatile memory, and the processor 102 can be a processor, microprocessor, controller, or a combination of processors, microprocessors, and/or controllers that performs instructions stored in memory 104. Such instructions stored in the memory 104, when executed by the processor, can direct the processor, to perform one or more features, functions, methods, and/or steps as described herein. Any input information or data can be stored in the memory 104—either the same memory or another memory. Additional physiological monitors 100 may include hardware and/or firmware that can include the instructions and/or perform these processes.

Certain monitors can include a networking device 106 to allow communication (wired, wireless, etc.) to another device, such as through a network, near-field communication, Bluetooth, infrared, radio frequency, and/or any other suitable communication system. A networking device 106 can be beneficial for receiving data, information, or input (e.g., structural data, sequence data, etc.) from another computing device and/or for transmitting data, information, or output (e.g., structural prediction) to another device. For example, some physiological monitors 100 relay audio or video input to a central device or server that is capable of recognizing specific noises into specific commands for a physiological monitor 100. However, certain physiological monitor 100 perform sound or video processing locally, to avoid consequences or concerns, should a loss of power or break in communications occur during monitoring. Certain physiological monitors 100 possess both options (e.g., performing processing locally and transmitting data remotely), as a form of redundancy—for example: audio and/or video data can be transmitted remotely for processing, but in the event of break in communication (e.g., due to power loss or other technical complication), processing can occur locally. While the advantage of local audio processing is discussed in the context of communications necessities, privacy concerns or laws regulating transmission of health data may also provide a basis for local or desire for local audio processing. Networking device 106 can be used to update a machine learning model, firmware, software, drivers, and/or other component of physiological monitor 100.

Further physiological monitors 100 may include one or more peripheral devices or components to aid in a monitoring process. Such peripheral components can include a display, an alarm (including audible and/or visible alarms), sensors (e.g., electrodes, catheters, etc.), output devices, user interface, any other relevant peripheral device or component, and combinations thereof. As a physiological monitor, some components can include a probe (including ultrasound), a camera, an electrode, a cuff, a thermometer, a sensor, a catheter, any other devices to properly monitor a physiological parameter of an individual, and combinations thereof—such physiological parameters can include temperature, blood pressure, blood flow, blood oxygenation, pulse, and/or any other relevant parameter for a particular operation or use. Some physiological monitors 100 can connect such devices via one or more input ports 108 or output ports 110. However, various physiological monitors 100 include such peripheral devices as an inherent or built-in portion of physiological monitors 100.

Further physiological monitors 100 include one or more contactless input devices 112 for contactless input, such as a microphone, camera (2D, 3D, etc.), LiDAR, and/or any other relevant device for obtaining voice, gesture, or other contactless input for commanding a physiological monitor 100 to perform an action or process. Further physiological monitors 100 include additional components known in the art to suit a physiological monitor 100 to a particular need, including graphics cards, graphics processing units (GPU), signal processing circuitry or components (e.g., analog—to digital converters, digital-to-analog converters, etc.), amplifiers, filters, any other component for a particular purpose and combinations thereof. Further physiological monitors 100 include a display unit with a graphical user interface to display the signal, derivative parameters, alerts (or alarms), and/or any user instructions or guidance that can be relevant in performing physiological monitoring.

Physiological monitors 100 can be housed in a single housing or in multiple housings that can be connected or joined via wired and/or wireless communication (e.g., via input ports 108 or output ports 110 and/or networking device 106). Multiple-housing units can be useful in situations where a contactless input device 112 may function better at a different position that may not be obtainable with a larger device.

Methods of Acting Based on Contactless Input

Figure 2:
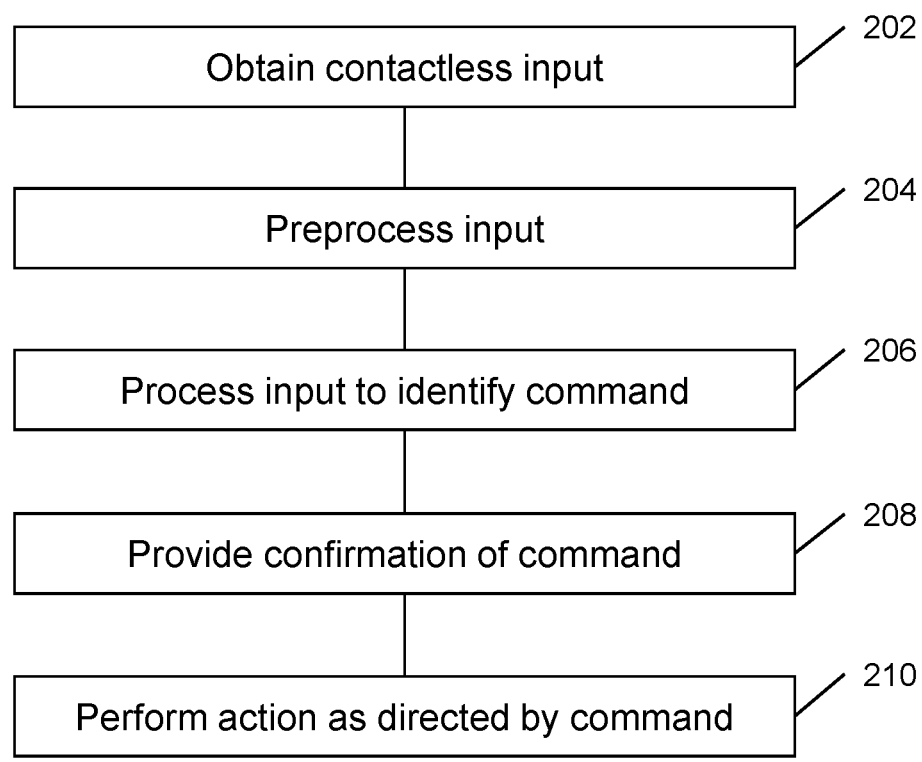
FIG. 2 illustrates a block diagram of an exemplary method for taking action based on contactless input in accordance with various implementations.

Various systems perform a variety of steps to take action based on a contactless input (e.g., voice and/or gesture). An exemplary method 200 for taking action is illustrated in FIG. 2. At 202, many methods obtain a contactless input from a user, such as a medical practitioner (e.g., nurse, physician, doctor, clinician, etc.). Such contactless input, as described herein, include voice commands, gesture commands, and/or other type of contactless input into a physiological monitor. As noted herein, some contactless input includes a series of two inputs: a triggering input and a command input, where a command input is an input for a desired command, action, or process to be undertaken by a physiological monitor, and the triggering input alerts the physiological monitor that a command input will follow.

Once a command is received, some methods 200 preprocess the contactless input 204. Preprocessing can include noise removal (e.g., background noise, cleaning up input, etc.).

At 206, various methods include processing the contactless input identify a command for the physiological monitor. Processing 206 can include voice recognition to identify an underlying command. For gesture based systems, processing can include object recognition, motion recognition, eyeball tracking, depth/distance measurement, and/or any other relevant information to identify a gesture (either in motion or stationary) from video of visual input. Various systems process the input locally (e.g., on the physiological monitor itself) or remotely (e.g., on a server or other central computing device). Remote devices can be housed within the same facility as the monitor or elsewhere in the world, including cloud-based or distributed systems.

Additional methods provide a confirmation or other receipt of a command at 208. Such confirmation can include confirming to a user (audibly and/or visibly) that the command was received, querying the user that command was received correctly (e.g., if the processing does not unambiguously identify the command), and/or providing a negative response that no valid command was received. In a situation of a negative response, some methods may provide troubleshooting to the user of the specific problem and/or how to resolve the issue. Alternatively, a negative response may provide a list of valid commands that may be provided at that time.

Further methods perform the action 210 as directed by the command. Such actions may be a singular action or providing a singular output, while other actions may be ongoing processes (e.g., monitoring).

It should be noted that method 200 is merely exemplary, and various methods may differ from what is described. For example, certain methods may include additional features, omit certain features, repeat certain features, and/or perform certain features in a different order than described herein. Additionally, certain features may be performed simultaneously or in an overlapping manner (e.g., start one feature before a separate feature is concluded).

Methods of Use

Figure 3:
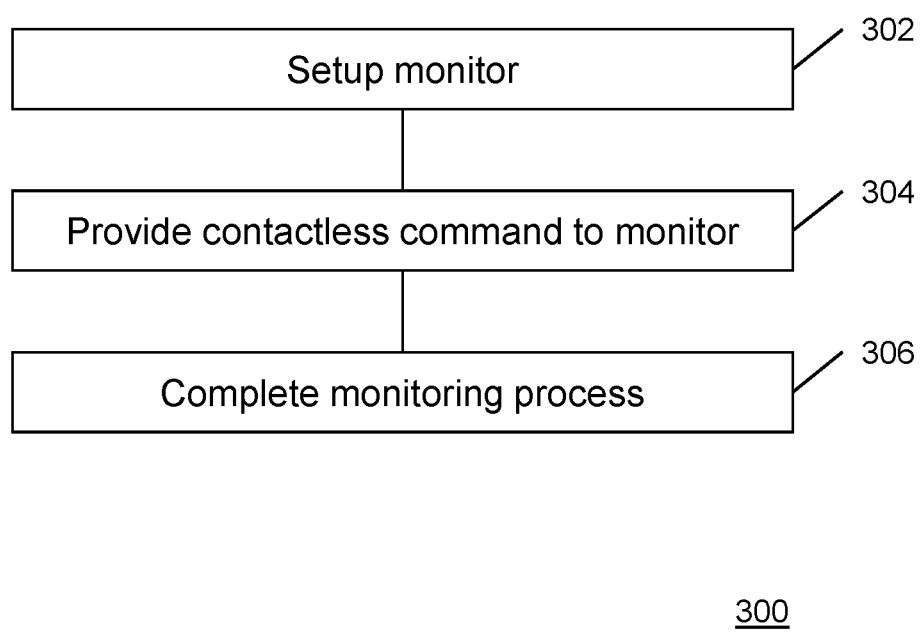
FIG. 3 illustrates a block diagram of an exemplary method for commanding a contactless physiological monitor in accordance with various implementations.

Further methods include directing a physiological monitor via voice and/or gesture command by a user, such as a medical practitioner (e.g., nurse, physician, doctor, clinician, etc.). Turning to FIG. 3, an exemplary method 300 for commanding a physiological monitor. In exemplary method 300, many methods setup a physiological monitor at 302. Setting up a monitor, as in 302, can include connecting sensors (e.g., electrodes, catheter, etc.) to an individual, connecting any sensors to the monitor, and/or connecting the monitor to a power source. In some methods 300, setup 302 includes calibrating any input devices, such as cameras, microphones, and/or sensors. Further methods 300 include connecting a physiological monitor to any central database or remote device, where data is stored and/or processed, such as when audio or visual data is processed on a different device than the physiological monitor.

At 304, certain methods 300 include providing a contactless input to a physiological monitor. As described herein, contactless inputs can include voice and/or gesture commands to the physiological monitor. In certain methods, contactless input includes a series of two inputs: a triggering input and a command input, where the triggering input causes the monitor to identify a command (e.g., voice, gesture, etc.) from the user, and the command input is a command for an action or process to be undertaken by the physiological monitor.

Further methods, complete monitoring an individual at 306. Completing monitoring can include removing any sensors (e.g., catheters, electrodes, etc.) from an individual, securing a physiological monitor, and/or any process to complete the a standard monitoring of an individual.

DOCTRINE OF EQUIVALENTS

Although the invention has been described in detail with particular reference to these preferred embodiments, other embodiments can achieve the same results. Variations and modifications of the present invention will be obvious to those skilled in the art and it is intended to cover all such modifications and equivalents. The entire disclosures of all references, applications, patents, and publications cited above, and of the corresponding application(s), are hereby incorporated by reference.

What is claimed is:

1. A contactless physiological monitor, comprising:
   one or more contactless input devices capable of obtaining audio or gesture data from a user;
   a processor configured to receive input data from one or more sensors configured to measure one or more physiological parameters of a patient;
   a display; and
   a memory comprising instructions to direct the processor to:
      obtain contactless inputs from the user via the contactless input device, wherein the contactless inputs comprise a first contactless input in the form of a triggering input followed by a second contactless input in the form of a command input, wherein the triggering input indicates that the second contactless input is the command input, and the command input provides a desired action to be performed by the display regarding input data received from the one or more sensors;
      process the first contactless input and determine that it is a triggering input;
      upon determining that the first contactless input is a triggering input, process the second contactless input into a command input;
      direct the processor to perform depth measurement on captured gesture-based input from the user;
      determine, using the depth measurement, that a proximity of the user to the display is beyond a threshold proximity;
      determine, based on the proximity being beyond the threshold proximity, that the display should operate in a first display mode configured to display cardiac metrics of a patient when a practitioner is performing a procedure;
      determine, based on the proximity being within the threshold proximity, that the display should operate in a second display mode configured to display a results summary relevant before or after a procedure; and
      control the display to display, in the first display mode, the cardiac metrics based on the input data from the one or more sensors and based on the command input.

2. The contactless physiological monitor of claim 1, wherein the one or more contactless input devices is configured to obtain audio input from the user.

3. The contactless physiological monitor of claim 1, wherein the one or more contactless input devices is a microphone.

4. The contactless physiological monitor of claim 3, wherein the memory further comprises instructions to process an audio signal into a voice command input.

5. The contactless physiological monitor of claim 4, wherein the memory further comprises instructions to preprocess the audio signal.

6. The contactless physiological monitor of claim 5, wherein the instructions to preprocess the signal comprises removing background noise from the audio signal.

7. The contactless physiological monitor of claim 1, wherein the one or more contactless input devices is a camera for capturing gesture-based input from the user.

8. The contactless physiological monitor of claim 7, wherein the camera is a 2D camera for capturing gesture-based input from the user.

9. The contactless physiological monitor of claim 7, wherein the camera is a 3D camera for capturing gesture-based input from the user.

10. The contactless physiological monitor of claim 9, wherein the memory further comprises instructions to track an eyeball of the user, wherein movement of the eyeball is configured to cause the display to move a cursor or pan a screen of the display, and wherein a pause in movement of the eyeball is configured to cause the display to enlarge a portion of a screen.

11. The contactless physiological monitor of claim 7, wherein the memory further comprises instructions to direct the processor to process a gesture-based input from the user.

12. The contactless physiological monitor of claim 11, wherein the instructions to process the gesture-based input from the user comprises object recognition.

13. The contactless physiological monitor of claim 7, wherein the camera captures eyeball movement of the user, and the memory further comprises instructions to direct the processor to perform eyeball tracking.

14. The contactless physiological monitor of claim 13, wherein the processor controls the display based on input from eyeball tracking based on one or more contexts associated with the display, where portions of the display relate to providing an input or a selection and other parts of the display relate to area that may be expanded for viewing.

15. The contactless physiological monitor of claim 1, wherein the one or more contactless input device is a LIDAR system for capturing gesture-based input from the user.

16. The contactless physiological monitor of claim 15, wherein the memory further comprises instructions to direct the processor to process the gesture-based input from the user.

17. The contactless physiological monitor of claim 16, wherein the instructions to process the gesture-based input from the user comprises object recognition.

18. The contactless physiological monitor of claim 15, wherein the memory further comprises instructions to direct the processor to perform depth measurement.

19. The contactless physiological monitor of claim 1, further comprising an alarm.

20. The contactless physiological monitor of claim 1, wherein the processor is configured to receive input data from a first sensor and a second sensor of the one or more sensors, where each sensor is configured to measure one or more physiological parameters of a patient, wherein the contactless input relates to input data received from the first sensor, and wherein the instructions are configured to direct the processor to control the display to display information based on the input data from the first sensor based on the command input.

21. The contactless physiological monitor of claim 1 further comprising an alarm, wherein the memory further comprises instructions to direct the processor such that when the alarm is activated, the processor processes the second contactless input into a command input to turn off the alarm.

22. A method, comprising:
receiving, at a display, input data from one or more sensors configured to measure one or more physiological parameters of a patient;
obtaining contactless inputs from a medical practitioner, wherein the contactless inputs comprise a first contactless input in the form of a triggering input followed by a second contactless input in the form of a command input, wherein the triggering input indicates that the second contactless input is the command input, and the command input provides a desired action to be performed by the display regarding input data received from the one or more sensors;
processing the first contactless input and determining that it is a triggering input;
upon determining that the first contactless input is a triggering input, processing the second contactless input as a command input from the medical practitioner;
performing depth measurement on captured gesture-based input from the medical practitioner;
determining, using the depth measurement, that a proximity of the medical practitioner to the display is beyond a threshold proximity;
determining, based on the proximity being beyond the threshold proximity, that the display should operate in a first display mode configured to display cardiac metrics of a patient when a practitioner is performing a procedure;
determining, based on the proximity being within the threshold proximity, that the display should operate in a second display mode configured to display a results summary relevant before or after a procedure; and
controlling the display to display, in the first display mode, the cardiac metrics based on the input data from the one or more sensors and based on the command input.

23. The contactless physiological monitor of claim 1, wherein the first contactless input is an audio input, and the second contactless input is a gesture, wherein upon determining that the first contactless input is a triggering input, said memory further comprises instructions to direct the processor to monitor the user for a gesture input.

24. The method of claim 22, further comprising:
tracking an eyeball of the medical practitioner, wherein movement of the eyeball is configured to cause the display to move a cursor or pan a screen of the display, and wherein a pause in movement of the eyeball is configured to cause the display to enlarge a portion of a screen.

25. The method of claim 24, wherein the contactless input is selected from audio input and gesture input.

26. The method of claim 24, further comprising preprocessing the contactless input.

27. The method of claim 26, wherein preprocessing the contactless input comprises removing background noise from an audio signal.

28. The method of claim 27, wherein the contactless input is gesture input and wherein processing the contactless input comprises performing a depth measurement on the gesture input.

29. The method of claim 28, wherein the contactless input is gesture input and wherein processing the contactless input comprises recognizing an object in the gestures input.

30. The method of claim 29, wherein the contactless input is gesture input and wherein processing the contactless input comprises performing eyeball tracking.

31. The method of claim 30, wherein the command input identified from the contactless input is selected from: change screens, configure parameters, configure alarm target ranges, silence alarms, create new patient session, input patient demographics, start monitoring, stop monitoring, calibrate, read out current parameters, scroll, adjust volume, set a timer, set a reminder, and display patient summary.

32. The method of claim 24, wherein receiving input data comprises receiving input from a first sensor and a second sensor of the one or more sensors, where each sensor is configured to measure one or more physiological parameters of a patient, wherein the contactless input relates to input data received from the first sensor, and wherein the controlling the procedural metrics comprises controlling the display to display information based on the input data from the first sensor based on the command input.

* * * * *